(12) United States Patent
Sakamoto et al.

(10) Patent No.: US 6,414,183 B1
(45) Date of Patent: Jul. 2, 2002

(54) METHOD FOR HANDLING WASTE OIL

(75) Inventors: Kazuhiko Sakamoto; Sei Nakahara; Masatoshi Ueoka, all of Himeji (JP)

(73) Assignee: Nippon Shokubai Co., Ltd., Osaka-fu (JP)

( * ) Notice: Subject to any disclaimer, the term of this patent is extended or adjusted under 35 U.S.C. 154(b) by 0 days.

(21) Appl. No.: 09/543,743

(22) Filed: Apr. 5, 2000

(30) Foreign Application Priority Data

Apr. 5, 1999 (JP) .......................................... 11-097993

(51) Int. Cl.$^7$ .............................................. C07C 69/54
(52) U.S. Cl. ..................... 560/218; 560/205; 560/210; 560/211; 560/212; 562/523; 562/531; 562/532; 562/533; 562/534; 562/544; 562/546; 562/547; 562/600; 562/535
(58) Field of Search ................................ 560/218, 205, 560/210, 211, 212; 562/523, 531–535, 544, 546, 547, 600

(56) References Cited

U.S. PATENT DOCUMENTS 4,365,081 A 12/1982 Shimizu et al. ............. 560/209

*Primary Examiner*—Paul J. Killos
*Assistant Examiner*—Robert W. Deemie
(74) *Attorney, Agent, or Firm*—Wenderoth, Lind, & Ponack, L.L.P.

(57) ABSTRACT

The present invention provides a method for stabilizing waste oil which is taken of each chemical apparatus of the manufacturing line of (meth)acryl acid and/or ester thereof, and treating the waste oil such as draining it out of the production apparatus, for example, a distillation tower from its bottom, sending and transporting it by a pump through a pipeline, and storing it in a storage tank in a simple manner while keeping the waste oil in a stable state. The waste oil can be stabilized by coexisting with solvent.

The solvent used in the present invention is typically at least one selected from the group consisting of water, alcohol, ether, carboxylic acid, ketone, aromatic hydrocarbons, and aliphatic hydrocarbons.

18 Claims, 3 Drawing Sheets

METHOD FOR HANDLING WASTE OIL

This application is based on patent application No. 11-97993 filed in Japan, the contents of which are hereby incorporated by references.

BACKGROUND OF THE INVENTION

1. Field of the Invention

The present invention relates to a method for handling waste oil which is to be taken out of a manufacturing line of (meth)acrylic acid and/or ester thereof. More specifically, the present invention relates to a method for stabilizing waste oil which is to be taken out of each chemical apparatus of the manufacturing line of (meth)acrylic acid and/or ester thereof.

2. Description of the Related Art

In a process of producing (meth)acrylic acid and/or ester thereof, stages such as distillation, extraction and crystallization are conducted for obtaining the (meth)acrylic acid and/or ester thereof by separating impurities from poor quality substance which is synthesized from raw material. In a stage of distillation, for example, waste oil (e.g. distillation residue) may be remained in a distillation apparatus (e.g. at the bottom of a distillation tower). The waste oil is drained through its bottom and treated as waste. In a process of producing acrylic acid for example, waste oil, which may be remained in a distillation apparatus (e.g. at the bottom of the distillation tower), contains undistilled acrylic acid in some amount, polymers of acrylic acid, and polymerization inhibitor accumulated after being used in the process of producing the acrylic acid. The waste oil is in the form similar to tar at an ordinary temperature. The waste oil is usually taken out of the distillation tower through its bottom, and is sent to a combustion apparatus where the waste oil is burned. Alternatively, the waste oil may be sent to a storage tank where the waste oil is stored for some time and sent through a pipeline to a combustion apparatus where the waste oil is burned. The waste oil may be viscous, and contains precipitates and polymerizable substances. The generated precipitates in the waste oil may attach to the inner surface of the distillation tower and/or of the pipeline, or the polymerizable substances in the waste oil may be polymerized in the distillation tower and in the pipeline which may cause clogging of the pipeline and affect the transportation of the waste oil thorough the pipeline and also adversely affect the drainage of the waste oil out of the distillation tower. The waste oil may be solidified in the storage tank which may arise difficulties in draining the waste oil out of the tank.

At this stage, no method has been suggested for solving the above-described problem, that is, a method for stabilizing the waste oil and handling it, such as draining it out of the distillation tower through its bottom, sending or transporting it through the pipeline, and storing it in the storage tank in a simple manner, while keeping the waste oil in a stable state.

Japanese Examined Patent Publication No. 60-43055 discloses a method for stabilizing a distillation residue liquid generated in the production of 2-hydroxyalkyl (meth) acrylate. This prior art method aims to prevent the distillation residue liquid from gelation which is taken place by ferric salt of organic carboxylic acid and complex salt of 2-hydroxylalkyl (meth)acrylate used as catalysts for addition reaction. For this purpose, at least one of water, acetic acid, salicylic acid, ethanol amines, and methanol is added to the distillation residue liquid. This method is effective in suppressing the gelation of the distillation residue liquid containing such catalysts. However, there is no description on the application of this method to the stabilization of waste oil (e.g. distillation residue oil) which is generated in the production of (meth)acrylic acid and its ester and contains no such catalysts.

An object of the present invention is to solve the above prior art problems and to provide a method for stabilizing waste oil without any problems.

SUMMARY OF THE INVENTION

As a result of studies, the present inventors have found a method for stabilizing waste oil which is to be drained from each chemical apparatus of a manufacturing line of (meth) acrylic acid and/or ester thereof.

The method which can solve above problems is to treat said waste oil which is to be taken out of each chemical apparatus of a manufacturing line of (meth)acrylic acid and/or ester thereof by coexisting with solvent.

DETAILED DESCRIPTION OF THE PREFERRED EMBODIMENTS OF THE INVENTION

Figure 1:
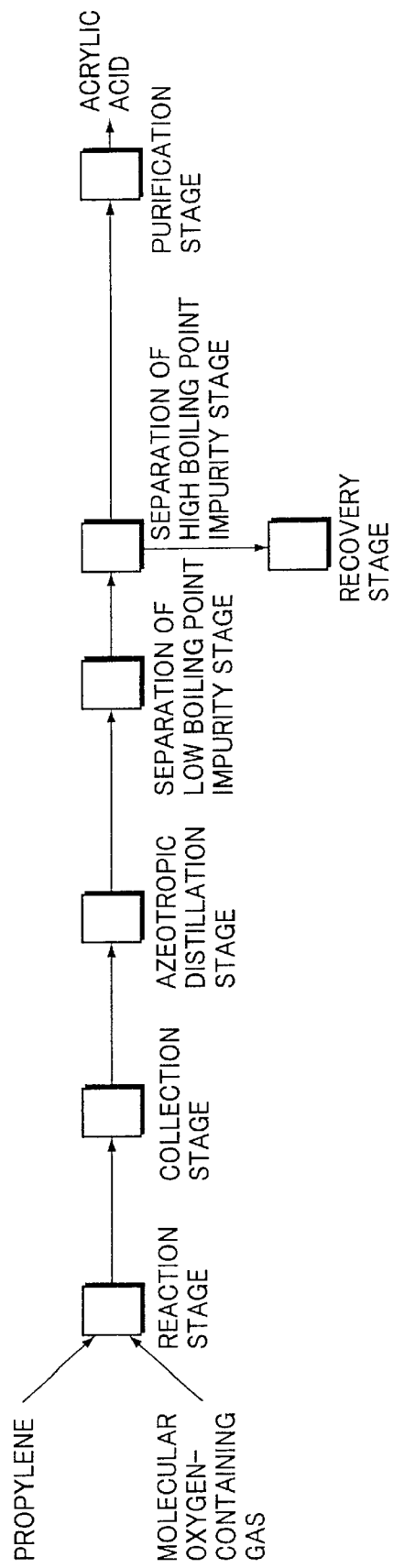
FIG. 1 is a schematic diagram of the manufacturing line of acrylic acid.

The present invention provide a method for preventing a polymerization of the waste oil and/or generation of precipitates in the waste oil for a long time by coexisting the waste oil with a solvent, when treating the waste oil, especially when taking the waste oil out of each chemical apparatus, pumping it by a pump, transporting it through a pipeline and storing it in a tank.

According to the present invention, (meth)acrylic acid and/or its ester include ,but not limited to, alkyl(meth) acrylates (i.e. methyl ester, ethyl ester, n-butyl ester and 2-ethyl hexyl ester of (meth)acrylic acid). The method of the present invention is preferable for treating waste oil which is to be drained from each chemical apparatus of a manufacturing line of (meth)acrylic acid and alkyl (meth)acrylate having 1 to 8 carbon atoms, and more preferably for treating waste oil which is to be drained from each chemical apparatus of a manufacturing line of (meth)acrylic acid and alkyl (meth)acrylate having 1 to 4 carbon atoms, and especially preferable for treating waste oil which is to be drained from each chemical apparatus of a manufacturing line of (meth) acrylic acid.

"manufacturing line", according to the present invention, means a series of manufacturing stages including collection, separation and distillation for obtaining specified substance by purifying raw material. A manufacturing line for producing acrylic acid, which is described later, may include series of stages for obtaining acrylic acid by purifying aqueous solution of acrylic acid which is obtained by oxidizing raw material. A manufacturing line can be exemplified in FIG. 1 which represents one of manufacturing lines of acrylic acid and in FIG. 2 which represents one of manufacturing lines of (meth)acrylate ester. However, the application of the present inventive method is not limited to the manufacturing line shown in these figures. The present inventive method can be also applicable to a manufacturing line of the above mentioned (meth)acrylic acid and/or ester thereof.

"waste oil", according to the present invention, means a liquid substance which is to be taken out of each chemical apparatus of a manufacturing line of (meth)acrylic acid and/or ester thereof. The waste oil may be the liquid which is taken out from the top of each chemical apparatus for separation stage and purification stage (e.g. a separation tower, a distillation tower and a vaporization tower) or may be the liquid, which may contain at least one selected from polymerizable substances, precipitates polymerization inhibitors, at the bottom of chemical apparatus.

"stability" (may be referred to as "stable state"), according to the present invention, means a state of the waste oil which is easily taken out of a chemical apparatus and/or storage tank without changing its phase from liquid phase to solid phase and also means a state of the waste oil which cause almost no solidification of the waste oil, polymerization of polymerizable substance in the waste oil nor formation of precipitates. "stability" can be attained even if the waste oil generates the precipitates in a the waste oil as long as the amount of the generated precipitates in the waste oil is small enough not to clog the pipeline and not to prevent drainage of the waste oil from each chemical apparatus such as separation tower, distillation tower and the like.

"each chemical apparatus", which consists of the manufacturing line of the present invention, include varieties of chemical apparatus such as distillation tower and separation tower which are used in the stage for separation, distillation. Specific examples of the chemical apparatus are described later using the production process of acrylic acid.

Figure 2:
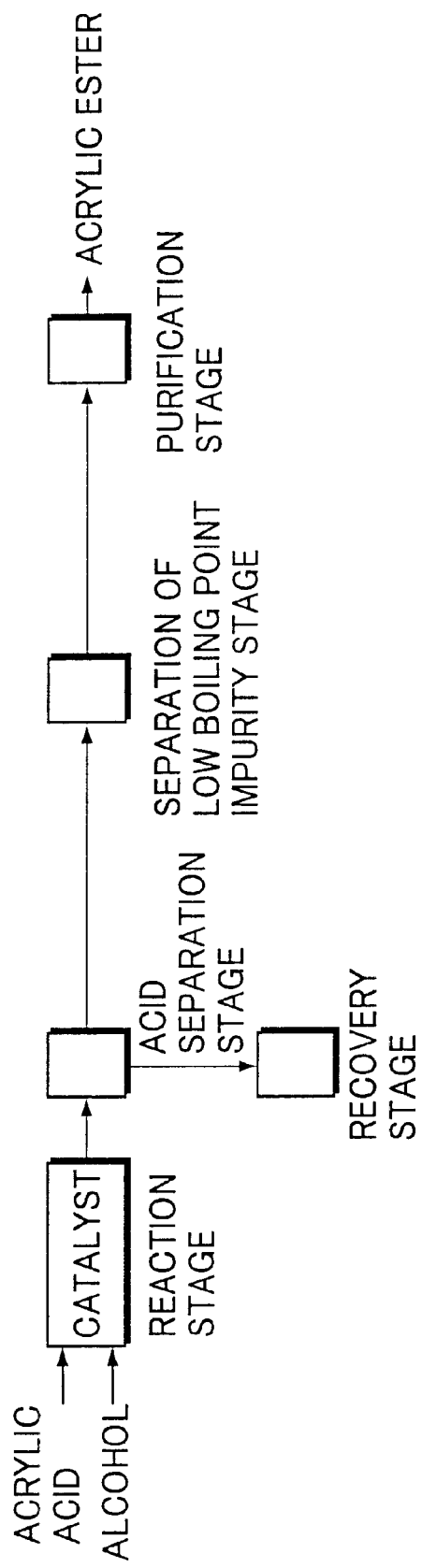
FIG. 2 is a schematic diagram of the manufacturing line of alkyl ester of acrylic acid.

The present invention will be further illustrated with reference to FIG. 1 and FIG. 2, which are schematic diagram of an embodiment of a manufacturing line for use in the present invention. It should be noted that the manufacturing lines of FIG. 1 and FIG. 2 are just an example of an manufacturing line usable in the method of the present invention, the present invention does not necessarily use these manufacturing lines and also noted that the method of the present invention can be applicable to a manufacturing line of the (meth)acrylic acid and/or ester thereof such as mentioned above.

First, the case of producing acrylic acid will be described with reference to FIG. 1. A mixed gas which is obtained by oxidizing propylene with a molecular oxygen-containing gas (reaction stage) is brought into contact with water to produce acrylic acid in the water (collection stage). The aqueous solution of acrylic acid is processed in azeotropic purification stage where the water is removed from the aqueous solution by azeotropic distillation by using such as a dewatering tower. After that, the resultant liquid is processed in separation of low boiling point impurity stage where impurities having low boiling points are removed by using such as a separation tower, and then is sent to separation of high boiling point impurity stage where impurities having a high boiling points are removed by using such as a separation tower. Then, thus obtained liquid is processed in purification stage where the liquid is purified by using such as a crystallizer and a distillation tower, and if necessary, is further sent to recovery stage where active principle of impurities having high boiling point is recovered by using such as a film evaporator. As a result of these stages, acrylic acid as a product is obtained.

The present invention can be applicable for stabilizing waste oil which is to be taken out of each chemical apparatus of the manufacturing line of (meth)acrylic acid and/or ester thereof, especially for stabilizing the waste oil which is to be taken out of each chemical apparatus for separation of high boiling point stage, purification stage and recovery stage.

Another method may be employed for producing acrylic acid. In the alternative method, a reaction gas generated by oxidizing propylene is brought into contact with a solvent having higher boiling point than acrylic acid such as diphenyl and diphenyl ether to produce the acrylic acid in the solvent. The acrylic acid-containing liquid is sent to the separation of low boiling point impurity stage, the separation of high boiling point impurity stage and the purification stage such as mentioned above, and if necessary, thus obtained liquid is sent to solvent stripping stage where the solvent having high boiling point such as diphenyl is recovered by using such as a stripping tower. As a result, acrylic acid as a product can be obtained.

The present invention can be applicable for stabilizing waste oil which is to be taken out of each chemical apparatus of the manufacturing line just mentioned above, especially for stabilizing the waste oil which is to be taken out of a chemical apparatus for the separation of high boiling point impurity stage, the purification stage and the solvent stripping stage.

Second, the case of producing (meth)acrylate ester will be described. In the production of methyl methacrylate among (meth)acrylic ester for example, esterification reaction of acrylic acid is conducted using strongly acidic ion exchange resin as a catalyst, and the resultant liquid is processed, in the stages such as shown in FIG. 2, in acid separation stage where the acid is separated from the resulted liquid, after that, the resultant liquid is processed in separation of low boiling point impurity stage where impurities having low boiling points are removed by using such as a separation tower, and then thus obtained liquid is processed in purification stage where the liquid is purified by using such as a crystallizer and a distillation tower, and if necessary, the acid containing liquid which is obtained from the acid separation stage may be sent to recovery stage where active principle in the separated acid is recovered by using such as a film evaporator. As a result of these stages, methyl methacrylate as a product is obtained.

Another example of the manufacturing line of (meth)acrylate ester is the production of butyl methacrylate. In the production of butyl methacrylate, esterification reaction of acrylic acid is conducted using sulfuric acid as a catalyst, and the resultant reaction mixture is processed in the separation stage and the distilled stage, and as a result of these stages, butyl methacrylate as a product is obtained.

Among the waste oil which is taken out of each chemical apparatus of the manufacturing line of (meth)acrylate ester, the present inventive method can be preferably applicable for stabilizing the waste oil which is to be taken out of the purification stage.

In the present invention, as a solvent for coexisting with the waste oil which is to be taken out of the each chemical apparatus mentioned above, the solvent which has compatibility with the waste oil and has capability of dissolving the precipitates in the waste oil may be preferably used. It is also possible to use a solvent having low compatibility with the waste oil and/or low ability of dissolving the precipitates as far as the waste oil keeps its stabile state. Typical examples of the solvent for coexisting with the waste oil include water, alcohol, ether, carboxylic acid, ketone, aliphatic hydrocarbon, and aromatic hydrocarbon.

Examples of the water as the solvent include industrial water, and waste water discharged from various plants as a result of production processes. Among them, waste water from plants, waste water from an ejector for example, may be economical and preferable.

Example of the alcohol used as the solvent is alcohol having 1 to 8 carbon atoms. Especially, methanol, ethanol, isopropyl alcohol, butanol, and 2-ethyl hexyl alcohol can be preferably used and methanol may be the most preferably used. These alcohol can be crude alcohol which may be industrially available at a low price. There is no need to specially prepare the alcohol for use as a solvent, but it is also possible to use the alcohol containing impurities and a mixture containing the alcohol which can be obtained from other plants.

Example of the ether as the solvent can be ether having 2 to 16 carbon atoms. Especially, dibutylether, anisole, diisoamyl ether, and diphyeny ether can be preferably used. These ethers may be crude ethers which are industrially available at a low price. It is also possible to use the ether containing impurities and a mixture containing the ether which can be obtained from other plants.

Example of the carboxylic acid as the solvent include acetic acid and propionic acid, and acetic acid is preferable. These carboxylic acids may be crude carboxylic acids which are industrially available at a low price. When acetic acid is used as the solvent, there is no need to specially prepare acetic acid for use as a solvent, but it is possible to use the acetic acid and the acetic acid-containing liquid which are separated in the production of acrylic acid as impurities.

Examples of the ketone as the solvent include acetone and methyl isobutyl ketone, and acetone is preferably used. These ketones may be crude ketones which are industrially available at a low price. There is no need to specifically prepare the ketone for use as a solvent, but it is possible to use the ketone containing impurities or a mixture containing the ketone which can be obtained from other plants.

Examples of the aliphatic and aromatic hydrocarbons as the solvent include hexane, heptane, toluene, xylene, diphenyl, and kerosene. These hydrocarbons may be crude aliphatic and aromatic hydrocarbons, and also may be a mixture containing the aliphatic or aromatic hydrocarbon. In addition, hydrocarbon of distilled middle and a heat-transfer oil having a boiling point of 170° C. or higher at normal pressure also may be used. Among them, kerosene is preferable.

Among the above-described solvents including exemplified solvents, it is industrially advantageous to use waste water which is discharged as a result of production processes such as waste water from an ejector, acetic acid and a liquid containing acetic acid which is generated as the impurities in the manufacturing line of the acrylic acid. Kerosene is also industrially advantageous, because kerosene works not only as the solvent but also as the origin of fire at the time of burning the waste oil.

The above-described solvents may be used alone or in combination with two or more of them. There is no specific limitation on a method for allowing the solvent to coexist with the waste oil, and the solvent can be added to the waste oil arbitrarily way. In the case of using the plural solvents, the solvents may be added separately or together at the same time.

There is no specific limitation on the position at which the solvent is added to the waste oil, for the manufacturing line of the (meth)acrylic acid and/or ester thereof for example, it can be recommended to add the solvent directly to the waste oil. Take the distillation tower and the film evaporator as examples of the chemical apparatus, it is preferable to introduced the solvent into the waste oil through a pipeline which may be used to drain the waste oil.

Upon coexisted with the solvent, the waste oil can be drained from the distillation tower through its bottom, can be sent through a pipeline and stored in a storage tank while being kept in a stable state.

Figure 3:
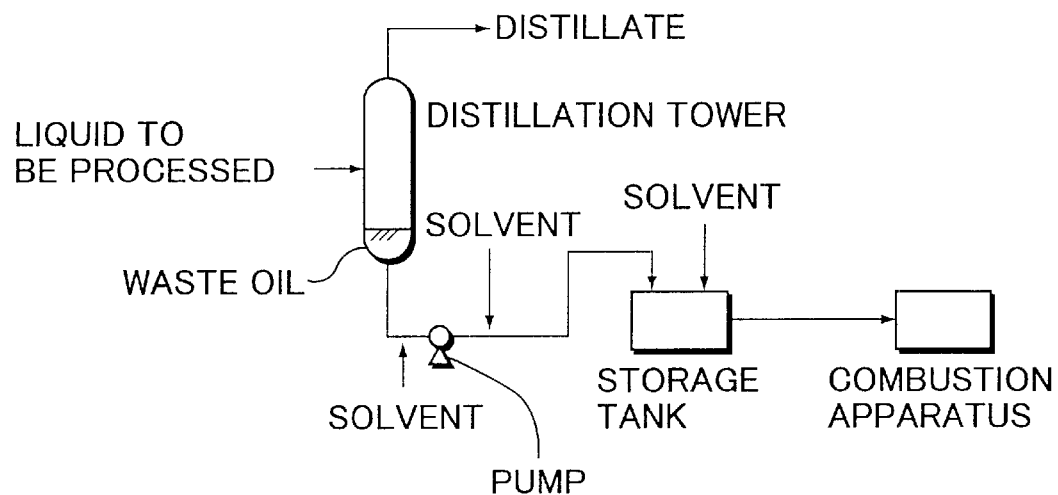
FIG. 3 is a schematic diagram of transportation of waste oil from distillation tower to storage tank.
Figure 4:
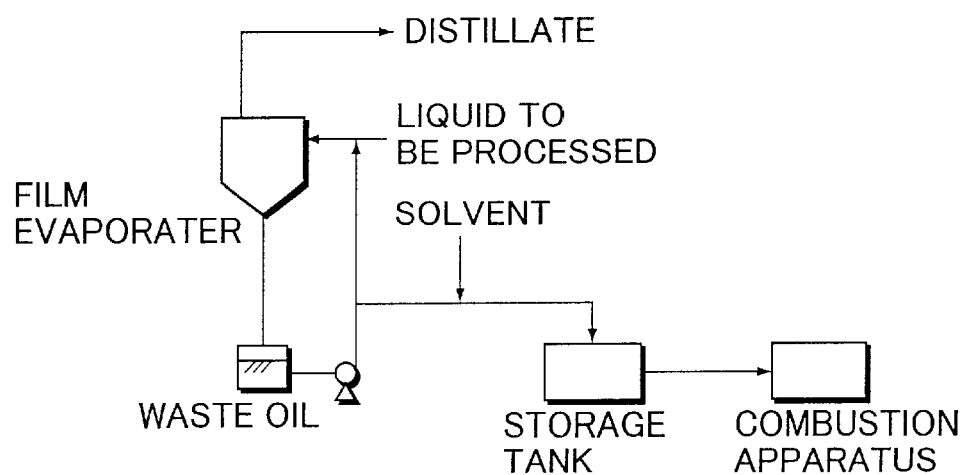
FIG. 4 is a schematic diagram of transportation of waste oil from film evaporator to combustion apparatus.

Alternatively, the solvent may be introduced into one or a plural positions of the pipeline installed before the combustion apparatus, such as shown in FIG. 3 and FIG. 4, so that the waste oil can be sent to the combustion apparatus while preventing the polymerization of the waste oil and preventing the generation of precipitates in the waste oil which may cause clogging of the pipeline. Accordingly, the stability of the waste oil is increased.

The solvent may be introduced into the storage tank so that the waste oil can be stored in a stable state for a long period of time without generating precipitates in the waste oil.

In addition, the solvent may be added to resulted liquid, which is obtained from one of stages of manufacturing line, and then the solvent-added liquid can be treated in the next stage. The solvent can be added to a liquid which is to be processed in the distillation tower for example, as far as the added-solvent does not impair the operation of the distillation tower and the quality of the distillate. In this case, it is necessary that the solvent can be easily separated from the (meth)acrylic acid or ester thereof by distillation. As the solvent which meets this requirement, it is preferable to use a solvent having a boiling point higher by 30° C. or more than that of the (meth)acrylic acid or the ester thereof to be treated at normal pressure.

The method of the present invention is applicable to other applications in addition to the treatment of the waste oil drained from the distillation tower or the film evaporator. For example, the method of the present invention is applicable to the treatment of the waste oil drained from a crystallization stage for use in the production of (meth) acrylic acid. When acrylic acid is crystallized by using such as a crystallizer, the crystallization operation may be conducted once or several times. As a result of the crystallization, residue in which impurities are concentrated is left. The residue is drained from the crystallizer as a waste oil, and this waste oil can be easily stabilized by applying the method of the present invention.

There is no limitation on the amount of the solvent for coexisting with the waste oil, but the amount of the solvent may be properly determined in consideration of the viscosity of the waste oil, of the features of the precipitates and of the amount of the precipitates contained in the waste oil. If the solvent is added to the waste oil excessively, the amount of the solvent added-waste oil is increased, and which leads to the increase of the energy consumption for burning it. Contrary to this, if the amount of the solvent added is not enough, the effect of coexisting the solvent with the waste oil, such as the stability of the waste oil, may not be attained. Preferable mass amount of the solvent to add to the waste oil may be within the range from 0.05 to 10, and more preferably from 0.1 to 5 times larger than the mass amount of the waste oil to be treated. The solvent added waste oil can be easily treated while being kept in a stable state if the amount of the solvent added is within this range.

In addition, it may be preferable to handle the waste oil, to which the solvent is added, at a temperature from 20 to 170° C., and preferably from 30 to 150° C. If the temperature of the waste oil is lower than 20° C., precipitates may be easily generated in the waste oil. If the temperature is higher than 170° C., the polymerizable substances in the waste oil may be polymerized.

There is no limitation on the viscosity of the waste oil which is to be treated by the present inventive method. The viscosity of the waste oil which is coexisted with the solvent may be preferably 200 cP or lower, more preferably 100 cP or lower, and the most preferably 50 cP or lower at the waste oil temperature of 100° C. For the waste oil which is to be taken out of the manufacturing line of the acrylic acid, the viscosity of the solvent added waste oil may be preferably 200 cP or lower, more preferably 100 cP or lower, and the most preferably 50 cP or lower at the waste oil temperature of 100° C. Along with the decrease of the viscosity, more preferable stability of the waste oil can be obtained.

According to the present invention, the waste oil which is to be taken out of each chemical apparatus of a manufacturing line of (meth)acrylic acid and/or ester thereof can be efficiently stabilized and also the waste oil can be treated easily while being kept in a stable state. Specifically, the effects of the present invention are as follows:

(1) The polymerization of the waste oil and generation of precipitates in the waste oil, for example the waste oil in the distillation tower, in the crystallizer, in the distillation tower and in the film evaporator, can be prevented. As a result, the waste oil can be drained from the chemical apparatus such as the distillation tower and film evaporator while being kept in a stable state without clogging a drainage pipe by the waste oil;

(2) When the waste oil is sent or transported through the pipeline by the pump, the polymerization of the waste oil and generation of precipitates in the waste oil never occur. As a result, the pump and pipeline are never clogged with the waste oil, and the waste oil can be sent and transported in a stable state; and (3) When the waste oil is stored in the storage tank, the polymerization of the waste oil and generation of precipitates in the waste oil can be effectively prevented. As a result, the waste oil can be stored in a stable state for a long period of time.

EXAMPLES

Hereinafter, the present invention will be described in detail by way of examples. However, the scope of the present invention is not limited to these examples.

Example 1

Propylene was oxidized to obtain a mixed gas, and the mixed gas was brought into contact with water to produce acrylic acid in the water. The acrylic acid aqueous solution was distilled and purified using an acrylic acid purification apparatus. As a result of these stages exemplified in FIG. 1, acrylic acid was obtained. In the production of the acrylic acid, the waste oil (containing 5.0 mass percent of acrylic acid), which was drained from purification stage (crystallizer and distillation tower) and recovery stage (film evaporator), was transported to a storage tank.

As shown in FIG. 3, the waste oil was drained through the bottom of the apparatus and sent to the tank through a pipeline by a pump. After the waste oil was introduced into the tank, acetic acid in an amount of 20 mass percent with respect to the waste oil was added to the waste oil and mixed. The mixture was heated to 100° C., and then, the mixture was transported through another pipeline by another pump at a speed of 1 kg/hour.

It was possible to continuously transport the waste oil in a stable state for 7 days. After 7 days, the transportation was stopped, the pumps and pipelines were overhauled and their inside states were checked. Neither viscous substance (e.g. polymerized substance) nor precipitates were attached inside the pump and pipeline.

Comparative Example 1

The waste oil was transported by repeating the steps of Example 1, except that no acetic acid was added to the waste oil. After 10 hours from the initiation of the transportation of the waste oil, the transportation became impossible. The pumps and pipelines were overhauled to check their insides states, and it was found that viscous substances and precipitates were attached inside the pumps and pipelines.

Comparative Example 2

The waste oil was transported by repeating the steps of Example 1, except that ethanol amine was used instead of acetic acid. After 10 hours from the initiation of the transportation of the waste oil, the transportation became impossible. The pumps and pipelines were overhauled to check their insides states, and it was found that viscous substances and precipitates were attached inside the pump and pipeline.

Example 2

The waste oil was transported by repeating the steps of Example 1, except that water was used instead of acetic acid. It was possible to continuously transport the waste oil in a stable state for 7 days. After 7 days, the transportation was stopped, the pump and pipeline were overhauled and their inside states were checked. Neither viscous substance nor precipitates were attached inside the pump and pipeline.

Example 3

Isobutylene was oxidized to obtain a mixed gas, and the mixed gas was brought into contact with water to produce methacrylic acid in the water. The methacrylic acid aqueous solution was purified using a methacrylic acid purification apparatus. As a result, methacrylic acid was obtained. In the production of the methacrylic acid, a waste oil containing 50 mass percent of meth acrylic acid, which was drained from distillation tower and a film evaporator, was transported to the storage tank. The waste oil was sent to the tank through a pipeline by a pump.

After the waster oil was introduced into the tank, methanol in an amount of 20 mass percent with respect to the waste oil was added to the waste oil and mixed. The mixture was heated to 50° C., and then, was transported through another pipeline by another pump at a speed of 1 kg/hour.

It was possible to continuously transport the waste oil in a stable state for 7 days. After the transportation was stopped, the pump and pipeline were overhauled and their inside states were checked. Neither viscous substance nor precipitates were attached inside the pump and pipeline.

Comparative Example 3

The waste oil was transported by repeating the steps of Example 3, except that no methanol was added to the waste oil. After 2 days from the initiation of the transportation, the transportation became impossible. The pump and pipeline were overhauled to check their insides states, and it was found that viscous substances and precipitates were attached inside the pump and pipeline.

What is claimed is:

1. A method for producing (meth)acrylic acid or ester thereof comprising:

providing a reaction gas generated by oxidizing propylene and/or acrolein in contact with a gas containing molecular state oxygen, or a reaction gas generated by oxidizing at least one member selected from isobutylene, t-butyl alcohol and methacrolein in contact with a gas containing molecular state oxygen;

treating the reaction gas to produce a (meth)acrylic acid solution; and purifying the (meth)acrylic acid solution to produce (meth)acrylic acid, wherein waste oil produced during the method and which contains (meth)acrylic acid or ester thereof is coexisted with a solvent.

2. A method according to claim 1, wherein the solvent is at least one selected from a group consisting of water, alcohol, ether, carboxylic acid, ketone, aromatic hydrocarbons and aliphatic hydrocarbons.

3. A method according to claim 2, wherein the water is industrial water and/or waste water discharged from various plants.

4. A method according to claim 2, wherein the alcohol is an alcohol having 1 to 8 carbons.

5. A method according to claim 2, wherein the ether is an ether having 2 to 16 carbon atoms.

6. A method according to claim 2, wherein the carboxylic acid is acetic acid and/or propionic acid.

7. A method according to claim 2, wherein the ketone is acetone and/or methyl isobutyl ketone.

8. A method according to claim 2, wherein the aromatic hydrocarbons and the aliphatic hydrocarbons is at least one selected from a group consisting of hexane, heptane, toluene, xylene, diphenyl, and kerosene.

9. A method according to claim 1, wherein the solvent is acetic acid and/or methanol.

10. A method according to claim 9, wherein the acetic acid is an acetic acid which is separated and recovered from the process stream of (meth)acrylic acid and/or ester thereof as impurities.

11. A method according to claim 1, wherein the mass amount of the solvent is from 0.05 to 10 times larger than the mass amount of the waste oil.

12. A method according to claim 1, wherein the solvent is added to the waste oil after the waste oil is taken out of a process stream.

13. A method according to claim 1, wherein the waste oil which coexisted with the solvent has a viscosity of 200 cP or less at 100° C.

14. A method according to claim 1, wherein the mixture of solvent and waste oil is processed in a chemical apparatus.

15. A method according to claim 14, wherein the boiling point of the solvent is higher by at least 30° C. than that of (meth)acrylic acid and/or ester thereof.

16. A method according to claim 15, wherein the solvent is diphenyl and/or diphenyl ether.

17. A method according to claim 1, wherein the reaction gas is treated with water to produce the (meth)acrylic acid solution.

18. A method according to claim 1, wherein the (meth) acrylic ester is a methyl ester, ethyl ester, n-butyl ester or 2-ethyl hexyl ester of (meth)acrylic acid produced by reacting (meth)acrylic acid and alcohol.

* * * * *